United States Patent [19]

Page et al.

[11] Patent Number: 4,617,188

[45] Date of Patent: Oct. 14, 1986

[54] NATURAL INSECTICIDES EMPLOYING BORAX AND CAROB

[75] Inventors: Edward J. Page, Bergenfield, N.J.; James E. Rock, Norfolk, Va.

[73] Assignee: O.U.T. Laboratories, Inc., Norfolk, Va.

[21] Appl. No.: 727,630

[22] Filed: Apr. 30, 1985

Related U.S. Application Data

[63] Continuation-in-part of Ser. No. 543,905, Oct. 20, 1983, abandoned.

[51] Int. Cl.$^4$ ...................... A01N 25/00; A01N 59/14
[52] U.S. Cl. ...................................... 424/148; 514/780
[58] Field of Search ................ 514/948, 780; 424/148, 424/84

[56] References Cited

U.S. PATENT DOCUMENTS

| | | | |
|---|---|---|---|
| 3,659,026 | 4/1972 | Schuppner | 424/361 |
| 3,996,378 | 12/1976 | Payton | 424/361 |
| 4,049,460 | 9/1977 | Broadbent | 424/84 |
| 4,107,292 | 8/1978 | Nemeth | 424/361 |

FOREIGN PATENT DOCUMENTS

| | | | |
|---|---|---|---|
| 978853 | 12/1975 | Canada | 424/148 |
| 4723198 | 10/1969 | Japan | 424/148 |
| 0008602 | of 1892 | United Kingdom | 424/148 |
| 0005705 | of 1897 | United Kingdom | 424/148 |
| 0013003 | of 1902 | United Kingdom | 424/148 |

OTHER PUBLICATIONS

W. Ebeling et al., 59, *J. of Economic Entomology*, (No. 6), 1374–1388, (1966).

*Primary Examiner*—Allen J. Robinson
*Attorney, Agent, or Firm*—Leydig, Voit & Mayer, Ltd.

[57] ABSTRACT

In abstract the present invention is a mixture of natural ingredients both mineral and vegetable whose combined effect is to kill insects such as cockroaches more effectively than can the components individually. When natural sugars are introduced through a medium such as carob which is not itself repulsive to the roaches, they increase the effectiveness of borax. The resulting compound can be used to eliminate roach populations in both domestic and commercial areas.

12 Claims, No Drawings

NATURAL INSECTICIDES EMPLOYING BORAX AND CAROB

This application is a continuation-in-part of application Ser. No. 543,905, filed 10/20/83, abandoned.

FIELD OF THE INVENTION

This invention relates to insect control through natural means and more particularly to improved natural insecticides.

BACKGROUND OF INVENTION

Man has been confounded by his inability to eliminate cockroaches from his domestic environment since history begain. Cockroaches are among the oldest fossil insects and the most primitive living, winged insects. They prefer humid, dark and warm areas to live. The German cockroach (blattella germanica) is the most common household pest and are sometimes called waterbugs. Three or more generations may occur yearly.

Hundreds of methods have been developed to rid the home of the determined cockroach, but cockroaches are still a major menace and difficult to keep in check. In the late 1800's borax was a common remedy because of its low cost and reasonably good results. Borax (sodium tetraborate) is a mineral found principally in the Western United States. This rock is processed for purity and ground into an ultra-fine powder. Sugar and chocolate was often added thinking the mixture would be attractive to the vermin, but both additives were found to actually be repellent. Borax can be improved through the addition of sugar which increases the effectiveness of borax in captive circumstances by up to four times. However, when the roaches were allowed to roam free, they regularly chose to stay away from the treated area thus rendering moot the increase in surface killing ability of the borax/sugar combination.

Todays concern for environmental safety, especially in the home, has brought about a renewed interest in oldtime solutions such as borax. Improvement of borax to make it at least equal to the killing effectiveness of commercial insecticides would create a product with little negative environmental impact while controlling the health hazzard, namely, cockroach infestation.

BRIEF DESCRIPTION OF INVENTION

After much research and study into the abovementioned problems, it has been discovered that vegetable additives which contain natural, unprocessed sugars improve the effectiveness of borax to control cockroach colonization in domestic areas while maintaining their attractiveness to cockroaches. The resulting combination improves the surface killing action of the borax while not repelling the roaches as do combinations of borax and processed cane sugar. If there is no contact, there can be no surface killing.

In view of the above, it is an object of the present invention to provide a vegetable material whose natural sugars can improve the effectiveness of borax as an insecticide while not repelling the quarry.

Another object of the present invention is to provide an effective means of controlling cockroaches which has only natural components.

Another object of the present invention is to provide a formulation which can satisfy EPA insecticide standards.

Another object of the present invention is to provide a long lasting cockroach control compound which only needs to be reapplied three or four times per year for consistant success.

Other objects and advantages of the present invention will become apparent and obvious from a study of the following description.

DETAILED DESCRIPTION OF THE INVENTION

A natural cockroach control compound is formed using borax as its primary active ingredient. The alkalinity of borax is pH 9.5, and this condition saponifies the acids and esters of the roaches lipids which in turn causes a water loss from the cuticle. The resulting moisture dissolves the borax which is most toxic to the surface of the insect when in solution. Adding sugar to the powdered mixture reduces the rate of evaporation because sugar does not give up the water very readily, and, therefore, the borax is allowed to remain active longer. When carob is used as the source of sugar rather than processed cane, the same long killing action is observed. Carob, however, is an attractant to cockroaches rather than a repellent as is processed sugar. Therefore, borax is improved not only in a captive situation, but also in real life situations.

Both borax and carob are hygroscopic, and when left exposed to the atmosphere will pick up moisture and cake. When caking occurs, the insects will not pick up the insecticide powder onto their bodies, and it is therefore useless. Cornstarch can be added to the mixture to absorb the moisture and serve as an anti-caking agent.

Captive battery jar tests were conducted at a major university using the most common "German cockroaches" with the following mortality results:

| MATERIAL TESTED | PERCENT DEAD | | |
| --- | --- | --- | --- |
| | WEEK 1 | WEEK 2 | WEEK 3 |
| Carob | 0.0 | 0.0 | 6.7 |
| Cornstarch | 0.0 | 0.0 | 0.0 |
| Borax | 33.3 | 96.7 | 100.0 |
| Boric acid | 93.3 | 100.0 | — |

Both carob and corn starch have no particular effect on cockroaches while borax is completely effective in the no-choice testing. However, boric acid is even faster than borax and is therefore the current choice in commercial products such as "ROACH PRUFE." All further testing has been compared to boric acid which is the stiffer test.

Boric acid is not used in the present invention because it is not enhanced through the introduction of sugar.

Carob is a Mediterranean bean which has become popular in "health foods" as a chocolate (cocoa bean) substitute. Carob flour is produced by roasting and grinding the pods of the carob tree, or as it also is known, the locust tree. Although carob flour is available widely on a commercial basis, it may be made directly from carob pods by methods well known in the art. In general, the pod is roasted at 300 to 600 degrees Fahrenheit for 5 to 15 minutes and ground into a powder. Conventional roasting and grinding equipment may be used.

The higher the roasting temperature, the shorter the roasting time, and vice versa. The selection of appropriate times and temperatures, however, will vary according to the pods which are to be roasted. As a natural product, there is some variation in carob pods, but as noted above, the roasting times and temperatures generally will vary within certain ranges.

Most importantly, however, the selection of appropriate roasting times and temperatures will vary according to the grade of carob desired. There are three principal grades of carob which are commercially available and recognized in the trade: raw or light roast, medium roast and dark roast. For the purposes of this patent application, a fourth grade, termed "superlight" roast, will be described. The selection of roasting variables, as suggested by the denomination of the grades, is determined largely by correlation to color changes.

Superlight roast is prepared by roasting the pods only to the degree necessary to enable their subsequent grinding into a powder, e.g., for 2–8 minutes at from 300 to 600 degrees Fahrenheit. The roasting should produce a flour which is a light beige or off-white color. Because the skin of the pod may vary in color, the superlight sometimes will have a very light pink or brown tint. This superlight carob flour will be sweeter than any of the three principal grades.

Raw or light roast is the sweetest and lightest of the principal grades, but it is darker and less sweet than superlight. It is roasted for a relatively short period of time, but somewhat longer than superlight, e.g., for 5 to 10 minutes at 300 to 600 degrees Fahrenheit. The natural color of the pod should not change dramatically, i.e., the flour should be a beige color. Light roast, because it generally contains 30 to 40 percent naturally occurring sugars, is used as a sweetening and flavoring agent for sugarless confections.

Medium roast is roasted longer than light roast. It is darker and less sweet. Generally, a medium roast can be produced by roasting the pods at 300 to 600 degrees Fahrenheit for 7 to 13 minutes but, in any event, the flour produced should be a light reddish brown. Medium roast is used as a carob coating for nuts and fruits and in other confections.

Dark roast is roasted longer than medium roast, e.g., at 300 to 600 degrees Fahrenheit for 10 to 15 minutes. It is a rich brown to red color, about the color of cocoa commonly sold for mixing in milk to produce chocolate milk. It is not as sweet as medium roast, but it is sweeter than cocoa. Thus, less sugar can be used in confections in which dark roast carob is substituted for cocoa.

Although, as described above, the various grades of carob flour may be produced directly from carob pods, they also are commercially available. For example, Famarco Limited, Inc., 1381 Air Rail Avenue, Virginia Beach, Va. 23455, markets dark, medium and light roast and, upon request, a superlight roast, under the trademarks FM-60, FM-40, FM-20, and FM-10, respectively.

Various compounds were mixed using 74% borax powder, 18% cornstarch, and 8% of carob flour in grades light, medium, and dark roast (FM-20, FM-40, and FM-60, respectively, obtained from Famarco Limited), and cocoa, respectively. The results were as follows:

| MATERIAL TESTED | PERCENT DEAD | | |
|---|---|---|---|
| | WEEK 1 | WEEK 2 | WEEK 3 |
| with FM-20 | 20.0 | 63.3 | 90.0 |
| with FM-40 | 20.0 | 53.3 | 80.0 |
| with FM-60 | 23.3 | 46.7 | 60.0 |
| with Cocoa | 6.7 | 43.3 | 66.7 |

A clear trend has been demonstrated with respect to the sweetness and amount of roasting of the carob and its respective benefit to the borax mixture. The sweetest, least roasted, FM-20 had almost perfect results while the FM-60 performed more poorly than cocoa. These results only record the pure killing power of the respective mixture and tend to discount the effect of choice.

When tested in choice box conditions, a mixture containing 74% borax, 8% superlight grade FM-10 carob and 18% cornstarch results in cockroach killing powers not only superior to its components individually, but also to those of other commercially available products as follows:

| MATERIAL TESTED | PERCENT DEAD | | |
|---|---|---|---|
| | WEEK 1 | WEEK 2 | WEEK 3 |
| Present Invention | 22.0 | 78.0 | 92.0 |
| Boric acid | 32.0 | 70.0 | 86.0 |
| "BAYGON" | 0.0 | 6.0 | 14.0 |

It is clear from the results that the mixture of 74% borax, 8% FM-10 and 18% cornstarch is vastly superior to the commercial product, "BAYGON" while maintaining some margin over the boric acid which has already been demonstrated to be superior to borax alone. These test results closely approximate real world conditions since the roaches could choose to enter the treated area or not.

Further experiments have been conducted in which the percentage of carob was varied from 4% to 12% without any appreciable change in the results.

From the above, it can be seen that the mixture of borax, corn starch and FM-10 carob produces results which are superior to any of the three components singularly, to other mixtures of less sweet carob or cocoa and to leading commercial products such as "BAYGON" and "ROACH PRUFE" (which is 99% boric acid).

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. An insecticide comprising an effective insecticidally amount of borax, as its active ingredient, and an effective amount of carob selected from the group consisting of superlight and light roast grade carob and mixtures therof, whereby the carob serves as an attractant.

2. The insecticide of claim 1, comprising 4 to 12% carob.

3. The insecticide of claim 1, comprising 8% carob.

4. The insecticide of claim 2, comprising cornstarch as an anticaking agent.

5. The insecticide of claim 3, comprising cornstarch as an anticaking agent.

6. The insecticide of claim 5, comprising 18% cornstarch.

7. A method for killing roaches which comprises applying an effective amount of an insecticidal mixture within an area infested by roaches, which mixture comprises an insecticidally effective amount of borax, as its active ingredient, and an effective amount of carob selected from the group consisting of superlight and light roast grade carob and mixtures thereof, whereby the carob serves as an attractant.

8. The method of claim 7, wherein the mixture comprises carob in an amount equal to 4 to 12% of total mixture.

9. The method of claim 7, wherein the mixture comprises carob in an amount equal to 8% of the total mixture.

10. The method of claim 8, wherein the mixture comprises cornstarch, whereby the cornstarch serves as an anticaking agent.

11. The method of claim 9, wherein the mixture comprises cornstarch, whereby the cornstarch serves as an anticaking agent.

12. The method of claim 11, wherein the mixture comprises cornstarch in an amount equal to 18% of the total composition.

* * * * *